US006534082B1

(12) United States Patent
Epstein

(10) Patent No.: US 6,534,082 B1
(45) Date of Patent: **\*Mar. 18, 2003**

(54) METHOD OF TREATING DISORDERS OF THE EYE

(75) Inventor: David L. Epstein, Bahama, NC (US)

(73) Assignee: Duke University, Durham, NC (US)

( * ) Notice: Subject to any disclaimer, the term of this patent is extended or adjusted under 35 U.S.C. 154(b) by 203 days.

This patent is subject to a terminal disclaimer.

(21) Appl. No.: 09/614,136

(22) Filed: Jul. 11, 2000

Related U.S. Application Data

(60) Continuation of application No. 08/442,652, filed on May 16, 1995, now Pat. No. 6,126,957, which is a division of application No. 08/180,482, filed on Jan. 12, 1994, now Pat. No. 5,458,883.

(51) Int. Cl.$^7$ .............................. A61K 9/00; A61K 9/06
(52) U.S. Cl. ....................... 424/427; 424/422; 514/438; 514/445; 514/569; 514/944
(58) Field of Search ................................ 424/427, 422; 514/438, 445, 569, 944, 969

(56) References Cited

U.S. PATENT DOCUMENTS

| | | | |
|---|---|---|---|
| 3,255,241 A | | 6/1966 | Schultz et al. |
| 3,758,506 A | | 9/1973 | Godfroid et al. |
| 4,094,983 A | * | 6/1978 | Bodor |
| 4,510,322 A | * | 4/1985 | Blaine ........................ 514/255 |
| 4,757,089 A | | 7/1988 | Epstein |
| 4,959,372 A | * | 9/1990 | Vincent ....................... 514/299 |
| 4,973,585 A | * | 11/1990 | Flynn ......................... 514/214 |
| 4,981,849 A | | 1/1991 | Ku |
| 5,073,641 A | | 12/1991 | Bundgaard et al. |
| 5,206,241 A | * | 4/1993 | Khandelwal .............. 514/232.8 |
| 5,306,731 A | | 4/1994 | Epstein |
| 5,332,582 A | | 7/1994 | Babcock et al. |
| 5,332,742 A | * | 7/1994 | Rosenberg .................. 514/253 |

FOREIGN PATENT DOCUMENTS

| | | |
|---|---|---|
| CA | 883792 | 10/1971 |
| GB | 1141422 | 1/1969 |
| WO | 86/07259 | * 12/1986 |
| WO | WO 95/33456 | 12/1995 |

OTHER PUBLICATIONS

Epstein et al, "Effect of iodoacetamide perfusion on outflow facility and metabolism of the trabecular meshwork", Investigative Ophthalmology & Visual Science, 20(5):625–631 (1981).
Epstein et al, "N–Ethylmaleimide Increases the Facility of Aqueous Outflow of Excised Monkey and Calf Eyes", Investigative Ophthalmology & Visual Science 22(6):752–756 (1982).
Erickson–Lamy et al, "Ethacrynic Acid Induces Reversible Shape and Cytoskeletal Changes in Cultured Cells", Investigative Ophthalmology & Visual Science 33(9):2631–2640 (1992).
Epstein et al, "Influence of Ethacrynic Acid on Outflow Facility in the Monkey and Calf Eye", Investigative Ophthalmology & Visual Science 28(12):2067–2075 (1987).
Tripathi et al, "Role of Receptors in the Trabecular Meshwork of the Eye as Targeted to the Development of Antiglaucoma Therapy", Drug Development Research 27:191–228 (1992).
Tripathi et al, "Use of Tissue Plasminogen Activator for Rapid Dissolution of Fibrin and Blood Clots in the Eye After Surgery for Glaucoma and Cataract in Humans", Drug Development REsearch 27:147–159 (1992).
Tingey et al, "Effects of Topical Ethacrynic Acid Adducts on Intraocular Pressure in Rabbits and Monkeys", Arch. Ophthalmol. 110:699–702 (1992).
Melamed et al, "The Effect of Intracamerally Injected Ethacrynic Acid on Intraocular Pressure in Patients With Glaucoma", Americal Journal of Ophthalmology 113:508–512 (1992).
Cyrlin et al, "Oral Ethacrynic Acid for the Treatment of Chronic Glaucoma", Invest. Ophthalmol. Vis. Sci. 33:(ARVO suppl):1121 (1992).
Epstein et al, "Thiol adducts of ethacrynic acid increase outflow facility in enucleated calf eyes", Current Eye Research 11(3):253–258 (1992).
Sarraf et al, "Transscleral Iontophoresis of Foscarnet", Invest. Ophthalmol. Vis. Sci. 24(ARVO suppl):1491 (1993).
Grossman et al, "Transscleral and Transcorneal Ionophoresis of Ketoconazole in the Rabbit Eye", Ophthalmology 96(5):724–748 (1989).
Magro et al, "Effect of Sulfhydryl–Reactive ATPase Inhibitors upon Mast Cell and Baslphil Activation", Int. Archs Allergy Appl. Immun. 72:41–45 (1993).
Scott et al, "Glutathione Peroxidase of Calf Trabecular Meshwork", Investigative Ophthalmology & Visual Science 25:599–602 (1984).
1 Pharmacodynamics 84:23 (1976)—Abstract.
Freddo et al, "Influence of Mercurial Sulfhydryl Agents on Aqueous Outflow Pathways in Enucleated Eyes", Investigative Ophthalmology & Visual Science 25:278–285 (1984).
Lindenmayer et al, "Morphology and Function of the Aqueous Outflow System in Monkey Eyes Perfused with Sulfhydryl Reagents", Investigative Ophthalmol & Visual Science 24:710–717 (1983).
Epstein et al, "The effect of diamide on lens glutathione and lens membrane function", Investigative Ophthalmology 9(8):629–638 (1970).
Kahn et al, "Glutathione in Calf Trabecular Meshwork and its Relation to Aqueous Human Outflow Facility", Investigative Ophthalmology & Visual Science 24:1283–1287 (1983).
Merck Index, 1983, #9273.
Peczon et al, "Diuretic Drugs In Glaucoma", American J. Ophthalmology 66:680–683 (1968).
Merck Index. #9273, 1983.*

* cited by examiner

*Primary Examiner*—Gollamudi S. Kishore
(74) *Attorney, Agent, or Firm*—Nixon & Vanderhye P.C.

(57) ABSTRACT

The present invention relates, in general, to methods of treating disorders of the eye, and, in particular, to methods of preventing or treating elevated eye pressure and glaucoma. The invention further relates to compounds and compositions suitable for use in such methods.

6 Claims, No Drawings

METHOD OF TREATING DISORDERS OF THE EYE

This application is a continuation of Ser. No. 08/442,652 filed May 16, 1995 now U.S. Pat. No. 6,126,957, which is a division of Ser. No. 08/180,482 filed Jan. 12, 1994 U.S. Pat. No. 5,458,883.

This invention was made, at least in part, with support from the National Eye Institute of the National Institutes of Health (Grant No. EY01894). The Government has certain rights in the invention.

TECHNICAL FIELD

The present invention relates, in general, to methods of treating disorders of the eye, and, in particular, to methods of treating diseases characterized by elevated intraocular pressure (ocular hypertension), such as glaucoma. The invention further relates to compounds and compositions suitable for use in such methods.

BACKGROUND

Glaucoma is a disease of the eye that is characterized by an elevation in intraocular pressure. The elevation in pressure results from an impairment in the outflow of aqueous humor from the anterior chamber of the eye via the trabecular meshwork (see Tripathi et al, Drug Develop. Res. 27:191 (1992)). Treatments for glaucoma focus on decreasing intraocular pressure and thereby avoiding damage to the optic nerve. Left untreated, glaucoma can lead to blindness.

Numerous agents have been used for the treatment of glaucoma, however, many are accompanied by undesirable side effects, such as ocular pain and localized allergy. Examples of such agents include adrenergic amine, epinephrine, and cholinesterase inhibitors. Although topical application is typically used, absorption of at least certain of these compounds can result in adverse systemic effects including headaches, nausea and the like.

U.S. Pat. No. 4,757,089 discloses a treatment for glaucoma that involves the administration to the eye of ethacrynic acid or analogs thereof that react with sulfhydryl groups of the trabecular meshwork of the eye. Erickson-Lamy et al (Invest. Opthalmol. Vis. Sci. 33:2631 (1992)) have reported that ethacrynic acid, acting via a SH-reactive mechanism, induces cytoskeletal changes that result in the observed physiologic effects on outflow facility. WO 92/16199 discloses an improvement in the method described in U.S. Pat. No. 4,757,089 that involves the use of agents that mask the sulfhydryl reactive site as the drug passes into the eye. The masking agent dissociates in the eye thereby freeing the sulfhydryl reactive site for interaction with the trabecular meshwork. Use of such masking agents prevents side effects (such as corneal edema) that occur in the absence of the masks. (See also Epstein et al, Current Eye Res. 11:253 (1992).)

The present invention provides a further approach to glaucoma treatment. The present method involves the use of compounds that increase aqueous humor outflow but are non-SH reactive. The mechanism of action of the present compounds would thus appear to be distinct from that of ethacrynic acid and the analogs thereof disclosed in U.S. Pat. No. 4,757,089 and WO 92/16199.

OBJECTS AND SUMMARY OF THE INVENTION

It is a general object of the invention to provide a method of treating disorders of the eye.

It is a specific object of the invention to provide a method of treating glaucoma, or elevated eye pressure, by increasing aqueous humor outflow.

It is another object of the invention to provide a method of preventing the onset of glaucoma, for example, following cataract surgery.

It is a further object of the invention to provide compounds and compositions suitable for use in preventing or treating glaucoma, or elevated eye pressure, and to provide container means that include same.

In one embodiment, the present invention relates to a method of lowering intraocular pressure in an eye of a warm-blooded animal in need of such treatment. The method comprises administering to the eye a non-sulfhydryl reactive derivative of phenoxyacetic acid capable of increasing aqueous humor outflow in an amount sufficient to effect the treatment.

In another embodiment, the present invention relates to a method of preventing the onset of glaucoma in an eye of a warm-blooded animal in need of such prevention. The method comprises administering to the eye a non-sulfhydryl reactive derivative of phenoxyacetic acid capable of increasing aqueous humor outflow in an amount sufficient to effect the prevention.

In a further embodiment, the present invention relates to a pharmaceutical composition comprising a non-sulhydryl reactive derivative of phenoxyacetic acid and a pharmaceutically acceptable carrier, wherein said composition is in the form of an ointment, cream or gel.

In yet another embodiment, the present invention relates to a container having disposed therewithin a solution of a non-sulfhydryl reactive derivative of phenoxyacetic acid that increases aqueous humor outflow, wherein the container includes an outlet means suitable for dispensing the solution from the container in droplets.

Further objects and advantages of the present invention will be clear from the description that follows.

DETAILED DESCRIPTION OF THE INVENTION

The present invention relates to methods of preventing and treating disorders of the eye characterized by elevated intraocular pressure, particularly, glaucoma. The present method results in an increase in aqueous humor outflow and thus a reduction in intraocular pressure that can be deleterious to the optic nerve.

Compounds suitable for use in the present method include non-SH-reactive phenoxyacetic acid derivatives, such as the anti-hypertensive agents indacrinone and ticrynafen, as well as non-SH-reactive derivatives thereof that increase aqueous humor outflow. The non-SH reactivity can be assessed, as described in the Examples below, by administering the compounds in combination with cysteine. Cysteine, which contains a reactive sulfhydryl group, has been shown in prior studies to be ineffective in influencing aqueous humor outflow. When administered in combination with ethacrynic acid, however, cysteine blocks the ability of that compound to increase outflow facility, thus indicating that ethacrynic acid exerts its effects by a sulfhydryl related mechanism (see U.S. Pat. No. 4,757,089). (See also Epstein et al, Current Eye Res. 11:253 (1992) and Tingey et al, Arch. Ophthal. 110:699 (1992)). Cysteine used in combination with non-sulfhydryl reactive phenoxyacetic acid derivatives does not block the ability of these compounds to increase outflow facility (see Examples).

Compounds suitable for use in the invention have a margin of safety of at least 2.0 and, advantageously, at least 4.0. That margin is measured as the ratio of the dosage of an aqueous humor outflow increasing compound that produces unacceptable side effects and the dosage that produces a clinically significant increase in aqueous humor outflow in a patient suffering advanced open angle glaucoma. Compounds suitable for use in the present method do not produce permanent or long term deleterious alterations in the eye.

The compounds of the invention can be formulated into compositions suitable for topical administration. Such compositions typically take the form of aqueous solutions that are administered dropwise to the eye. Alternatively, the compounds can be formulated into gels, ointments or creams that can be applied topically to the tissue surrounding the eye. The compounds of the invention can also be formulated into sterile solutions for administration by intracameral injection into the anterior chamber of the eye, for example, at the time of cataract surgery in order to avoid the postoperative onset of glaucoma. Administration by direct injection into the trabecular meshwork of the eye can also be effective (by way of example, see Melamed et al, Am. J. Ophthal. 113:508 (1992)). The compounds of the invention can also be administered to the eye by iontophoresis (see, for example, Grossman and Lee, Ophthalmology 96:724 (1989); Sarraf et al, Amer. J. Ophthal. 115:748 (1993); Sarraf et al, Invest. Ophthalmol. Vis. Sci. 34 (ARVO Suppl): 1491 (1993)). Systemic administration of the compounds of the invention is also contemplated, either oral administration or intravenous administration. In the case of oral administration, a suitable composition is in dosage unit form and is a pill, capsule, tablet or the like. Compositions suitable for intravenous administration are typically formulated as sterile solutions.

Whatever the mode of administration, the compositions of the invention include, as active agent, the non-SH-reactive phenoxyacetic acid derivative, and a pharmaceutically acceptable carrier. The compositions of the invention can also include agents that promote or enhance delivery, such as surfactants and wetting agents, benzalkonium being one such agent. The compositions can also include preservatives that prolong shelf life.

The amount of active agent to be included in the composition will vary with the phenoxyacetic acid derivative, with the dosage regimen used and with the effect sought. Preferred concentrations can be readily determined. Likewise, the optimum amount of phenoxyacetic acid derivative to be administered to any particular patient can be determined without undue experimentation.

The compounds and compositions of the invention can be provided in various container means. Compositions to be administered topically can be provided as sterile solutions in a container means that facilitates administration of the solution to the eye in drops. For example, the container means can include an outlet that allows for the dispensing of drops directly or, alternatively, the container means can include a separate dropper means reversibly associated therewith. Compositions to be administered topically that are formulated as creams, gels or ointments can be provided in container means that facilitate administration to the eye or surrounding tissue. Compositions to be administered by injection, intravenously or into the eye or surrounding tissue, can be provided as solutions in sterile container means.

The compounds and compositions of the invention are suitable for use in any mammal suffering glaucoma. While human treatment is the focus of the invention, veterinary use is also contemplated.

Certain aspects of the invention are described in greater detail in the non-limiting Examples that follow. Techniques used in the Examples are described in one or more of Erickson-Lamy et al, Invest. Ophthal. Vis. Sci. 33:2631 (1992), Epstein et al, Invest. Ophthal. Vis. Sci. 22:752 (1982), and Epstein et al Invest. Ophthal. Vis. Sci. 20:625 (1981). Prior studies with ethacrynic acid have demonstrated that the results obtained using the bovine eye model referenced in these publications (and in the Examples below) are predictive of comparable effects in vivo (eg in monkeys).

EXAMPLES

The experimental protocols that follow are utilized in the specific Examples set forth below:

Enunciated cow eyes were obtained from a local commercial abattoir, immediately chilled, and then perfused within twenty-four hours using a standard constant pressure perfusion technique. Pairs of eyes from a single animal were used for each experiment and subjected to the same manipulation except for the experimental drug in the experimental eye of perfusion. Briefly, a 5 mm central cornea trephine button was removed from each eye. Radial iridotomy was performed to prevent artificial deepening of the anterior chamber during perfusion. The anterior chamber was then gently irrigated with perfusion medium to remove pigment which might have been liberated by the iridotomy. A Grant stainless steel fitting was then placed into the cornea and connected by twenty-three gauge polyethylene tubing to the fluid reservoir of the perfusion apparatus.

The perfusion medium was Dulbecco's phosphate-buffered salt solution (PBS) (Grand Island Biological Company, Grand Island, N.Y.) with added 5.5 mM glucose. All solutions were filtered through a 0.2 $\mu$m Nuclepore filter.

The initial flow value was determined after the eyes had been perfused for one hour which allowed sufficient time to achieve adequate stability. The corneal fitting was removed, and the anterior chamber was gently emptied and refilled with fresh perfusion medium with added drug or sham solution. The corneal fitting was replaced and the eye was perfused for an additional five hours. The outflow facility (flow/pressure) was calculated at the end of the experiment and compared to the initial baseline after the initial hour (pre-drug, both eyes received control perfusion medium for the first hour). The change in the experimental eye was compared to the change in the fellow control eye by a paired T-test. Control eyes were treated similarly except that an osmotically equivalent amount of sodium chloride was added to the perfusion medium in place of the drug. All perfusions were performed at 22° centigrade and the perfusion pressure was 15 mm of mercury.

Example I

Treatment of Bovine Eyes with Indacrinone

Ten pairs of enucleated cow eyes were perfused with 0.125 mM indacrinone versus sham control. The baseline outflow facilities (microliters per minute per millimeter mercury pressure) were 2.35±0.20 (SEM) in the control eye versus 2.21±0.19 in the experimental indacrinone eye. At the end of the experiment, outflow facility had increased 43%±6% in the control eye, versus 113%±24% in the indacrinone treated eye. This was statistically significant at p<0.01.

In a separate set of experiments, six pairs of cow eyes were perfused with 0.125 mM indacrinone plus 0.625 mM cysteine (Sigma Chemical Company, St. Louis, Mo.) versus sham-manipulated control. The control contained an osmotically equivalent amount of sodium chloride. In these six pairs of eyes, outflow facility was 2.25±0.09 in the control eyes and 2.42±0.23 in the experimental indacrinone/cysteine treated eyes. At the end of the experiment, outflow facility had increased 52%±7 in the control eye and 91%±8 in the experimental indacrinone/cysteine eyes. The paired T-test indicated that this was highly significant increase in outflow facility with a p value of less than 0.005.

Example II

Treatment of Bovine Eyes with Ticrynafen

Six pairs of cow eyes were perfused with 0.125 mM ticrynafen versus sham. Baseline outflow facility was 2.28±0.24 in the control eyes and 1.87±0.41 in the experimental ticrynafen eyes. At the end of the perfusion period, outflow facility had increases 50%±20% in the control eyes and 102%±23% in the experimental ticrynafen treated eyes. The p value indicated a significance at less than 0.025.

In a separate experiment, six additional pairs of cow eyes were perfused with 0.125 mM ticrynafen with added 0.625 mM cysteine versus sham (sodium chloride added) treated eyes. The control eyes outflow facility was 3.12±0.18 and the experimental outflow facility was 3.19±0.11. At the end of the perfusion period, the control eyes had increased 32%±11% whereas the 0.125 mM ticrynafen/0.625 mM cysteine eyes had increased 80%±9%. This was highly significant with a p value less than 0.01, indicating a facility increase with this combination.

All documents cited above are hereby incorporated in their entirety by reference.

One skilled in the art will appreciate from a reading of this disclosure that various changes in form and detail can be made without departing from the true scope of the invention.

What is claimed is:

1. A method of lowering intraocular pressure in an eye of a warm-blooded animal in need of such treatment consisting essentially of administering to said eye a non-sulfhydryl reactive derivative of phenoxyacetic acid that increases aqueous humor outflow in an amount sufficient to effect said treatment.

2. The method according to claim 1 wherein said derivative is indacrinone, or non-sulfhydryl reactive analog thereof that increases aqueous humor outflow.

3. The method according to claim 1 wherein said derivative is ticrynafen, or non-sulfhydryl reactive analog thereof that increases aqueous humor outflow.

4. The method according to claim 1 wherein said derivative is administered topically to said eye.

5. The method according to claim 1 wherein said derivative is injected into said eye or surrounding tissue.

6. The method according to claim 5 wherein said derivative is injected into the anterior chamber or trabecular meshwork of said eye.

* * * * *